(12) United States Patent
Colbeth et al.

(10) Patent No.: US 7,123,687 B2
(45) Date of Patent: Oct. 17, 2006

(54) METHOD FOR DISPLAYING DIGITAL X-RAY IMAGE DATA AT HIGH RESOLUTION

(75) Inventors: Richard E. Colbeth, Los Altos, CA (US); Ivan P. Mollov, Cupertino, CA (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 49 days.

(21) Appl. No.: 10/410,819

(22) Filed: Apr. 10, 2003

(65) Prior Publication Data

US 2004/0202281 A1    Oct. 14, 2004

(51) Int. Cl.
*H05G 1/64* (2006.01)
(52) U.S. Cl. .................. 378/98.8; 378/19; 250/370.09
(58) Field of Classification Search ........... 250/370.09, 250/370.11; 378/19, 98.8
See application file for complete search history.

(56) References Cited

U.S. PATENT DOCUMENTS

| | | | | |
|---|---|---|---|---|
| 5,027,380 A * | 6/1991 | Nishiki | ........................ | 378/4 |
| 5,355,309 A * | 10/1994 | Eberhard et al. | ............. | 378/15 |
| 5,436,952 A * | 7/1995 | Haendle et al. | ............ | 378/98.7 |
| 5,452,338 A * | 9/1995 | Granfors et al. | ......... | 378/98.11 |
| 5,530,238 A * | 6/1996 | Meulenbrugge et al. | . | 250/208.1 |
| 5,715,292 A * | 2/1998 | Sayag et al. | ................ | 378/98.8 |
| 5,923,722 A * | 7/1999 | Schulz | ....................... | 378/98.8 |
| 6,028,913 A * | 2/2000 | Meulenbrugge et al. | ... | 378/98.8 |
| 6,330,302 B1 * | 12/2001 | Joosten | .................... | 378/98.12 |
| 6,333,963 B1 * | 12/2001 | Kaifu et al. | ................ | 378/98.2 |
| 6,343,112 B1 * | 1/2002 | Petrick et al. | ............. | 378/98.9 |
| 6,351,519 B1 * | 2/2002 | Bonk et al. | ................ | 378/98.8 |
| 6,453,008 B1 * | 9/2002 | Sakaguchi et al. | ......... | 378/98.7 |
| 6,459,765 B1 * | 10/2002 | Ganin et al. | ................ | 378/108 |
| 6,658,082 B1 * | 12/2003 | Okumura et al. | ............. | 378/19 |
| 6,823,044 B1 * | 11/2004 | Rosner | ...................... | 378/98.8 |
| 6,855,937 B1 * | 2/2005 | Tashiro et al. | ......... | 250/370.11 |
| 6,895,077 B1 * | 5/2005 | Karellas et al. | ............ | 378/98.3 |
| 7,010,091 B1 * | 3/2006 | Hayashida et al. | ........ | 378/98.8 |

OTHER PUBLICATIONS

International Search Report and Written Opinion dated Mar. 18, 2005, for International application PCT/US04/02558.
International Preliminary Report on Patentability, date of mailing Sep. 28, 2005.

* cited by examiner

*Primary Examiner*—Edward J. Glick
*Assistant Examiner*—Thomas R Artman
(74) *Attorney, Agent, or Firm*—Vedder, Price, Kaufman & Kammholz

(57) ABSTRACT

A method for providing X-ray image data signals corresponding to a selected portion of a two-dimensional image at an enhanced image resolution. During selective exposure of an X-ray receptor to X-ray radiation corresponding to the subject image, image pixel data corresponding to the region of interest (used pixels) are read out with normal pixel data pixel discharge times and at the normal pixel data rate, while image pixel data corresponding to the region not of interest (unused pixels) are read out also with normal pixel data pixel discharge times and at either the normal pixel data rate or an increased pixel data rate. During such pixel data readout intervals, the X-ray radiation exposure can be continuous or selectively pulsed.

10 Claims, 10 Drawing Sheets

METHOD FOR DISPLAYING DIGITAL X-RAY IMAGE DATA AT HIGH RESOLUTION

BACKGROUND OF THE INVENTION

The present invention relates to X-ray radiation imaging systems, and in particular, to solid state X-ray radiation imaging systems capable of operating in multiple detection and display modes, including magnification.

DESCRIPTION OF THE RELATED ART

The use of X-ray radiation has become a valuable and widespread tool in medical diagnoses and treatments. In film radiography, a burst of X-rays, after passing through the body, is recorded on high resolution X-ray film. In fluoroscopy, an image intensifier tube converts X-ray radiation to a video signal for viewing and recording interior body activity as a video image.

Film radiography is commonly used due to its good spatial resolution, high signal-to-noise ratio (SNR), large detection area and low cost. However, developing exposed X-ray film typically takes a minimum of ninety seconds which can be too long in emergency situations. Further, the relatively low dynamic range of X-ray film can result in under- or over-exposed images and, therefore, necessitate additional exposures which increase the aforementioned time delay as well as the X-ray dosage received by the patient.

The image intensifier tube used in fluoroscopy has a greater exposure latitude than X-ray film, but also has a more limited active detection area and lower spatial resolution. The lower spatial resolution associated with the total active area is somewhat mitigated in that the image intensifier tubes allow magnification of the central image portion, thereby providing a means to enhance visual details. However, the image intensifier tube is typically heavy, bulky and expensive, and can introduce image distortion which can only be partially removed during post processing.

A number of alternative X-ray imaging technologies have been developed. For example, one alternative, known as computed radiography, involves the use of a photostimulable phosphor plate which has the same physical appearance as a standard X-ray film cassette and provides good spatial resolution, SNR and dynamic range. However, after exposure to X-rays, the photostimulable phosphor plate must be scanned with a laser system which is large and expensive, and the readout process is just as slow as the development of film.

Another alternative which provides good spatial resolution and dynamic range, as well as the added advantage of compatibility with real time digital image processing techniques, involves the use of solid state detector panels. One such panel uses an amorphous silicon (a-Si) detector array arranged as a two dimensional matrix of pixels, each of which consists of a photosensitive element and a transistor switch. As with X-ray film cassettes, the detector array is covered with a scintillation layer to convert impinging X-rays into visible light for the photosensitive elements.

SUMMARY OF THE INVENTION

A method in accordance with the presently claimed invention provides X-ray image data signals corresponding to a selected portion of a two-dimensional image at an enhanced image resolution. During selective exposure of an X-ray receptor to X-ray radiation corresponding to the subject image, image pixel data corresponding to the region of interest (used pixels) are read out with normal pixel data discharge times and at the normal pixel data rate, while image pixel data corresponding to the region not of interest (unused pixels) are read out also with normal pixel data discharge times and at either the normal pixel data rate or an increased pixel data rate. During such pixel data readout intervals, the X-ray radiation exposure can be continuous or selectively pulsed.

In accordance with one embodiment of the presently claimed invention, a method for providing X-ray image data signals corresponding to a selected portion of a two-dimensional image at an enhanced image resolution includes:

exposing an X-ray receptor to a first amount of X-ray radiation during a first time interval;

reading out, from the X-ray receptor at a first data rate during the first time interval, a first plurality of pixel data signals corresponding to at least a first portion of a two-dimensional image and having a first pixel discharge time associated therewith;

exposing the X-ray receptor to a second amount of X-ray radiation corresponding to the two-dimensional image during at least a portion of a second time interval;

reading out, from the X-ray receptor at a second data rate during the second time interval, a second plurality of pixel data signals corresponding to at least a second portion of the two-dimensional image and having a second pixel discharge time associated therewith, wherein said first and second pixel discharge times are substantially equal; and converting the first plurality of pixel data signals to a plurality of video image signals suitable for displaying via an image display device at least a subordinate portion of the first portion of the two-dimensional image.

In accordance with another embodiment of the presently claimed invention, a method for providing X-ray image data signals corresponding to a selected portion of a two-dimensional image at an enhanced image resolution includes:

exposing an X-ray receptor to a first amount of X-ray radiation corresponding to a two-dimensional image during at least a portion of a first time interval and a second amount of X-ray radiation during a second time interval;

reading out, from the X-ray receptor at a first data rate during the first time interval, a first plurality of pixel data signals corresponding to at least a first portion of the two-dimensional image and having a first pixel discharge time associated therewith;

reading out, from the X-ray receptor at a second data rate during the second time interval, a second plurality of pixel data signals corresponding to at least a second portion of the two-dimensional image and having a second pixel discharge time associated therewith, wherein said first and second pixel discharge times are substantially equal; and converting the second plurality of pixel data signals to a plurality of video image signals suitable for displaying via an image display device at least a subordinate portion of the second portion of the two-dimensional image.

DETAILED DESCRIPTION OF THE INVENTION

The following detailed description is of example embodiments of the presently claimed invention with references to the accompanying drawings. Such description is intended to be illustrative and not limiting with respect to the scope of the present invention. Such embodiments are described in sufficient detail to enable one of ordinary skill in the art to practice the subject invention, and it will be understood that other embodiments may be practiced with some variations without departing from the spirit or scope of the subject invention.

Throughout the present disclosure, absent a clear indication to the contrary from the context, it will be understood that individual circuit elements as described may be singular or plural in number. For example, the terms "circuit" and "circuitry" may include either a single component or a plurality of components, which are either active and/or passive and are connected or otherwise coupled together to provide the described function. Additionally, the term "signal" may refer to one or more currents, one or more voltages, or a data signal. Within the drawings, like or related elements will have like or related alpha, numeric or alphanumeric designators. Further, while the present invention has been discussed in the context of implementations using discrete electronic circuitry (preferably in the form of one or more integrated circuit chips), the functions of any part of such circuitry may alternatively be implemented using one or more appropriately programmed processors, depending upon the signal frequencies or data rates to be processed.

Figure 1:
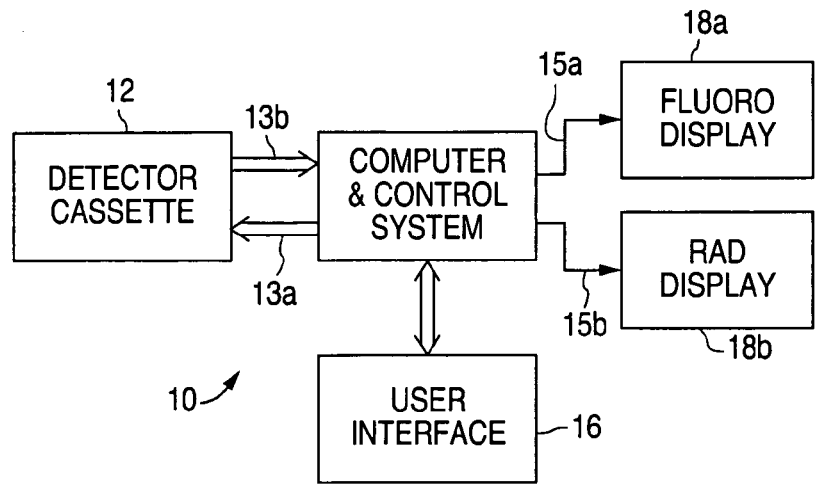
FIG. 1 is a functional block diagram of an X-ray imaging system in accordance with the present invention.

Referring to FIG. 1, an X-ray imaging system 10 in accordance with the present invention includes a detector cassette 12, a computer and control system 14, a user interface 16, a fluoroscopic display 18a and a radiographic display 18b, interconnected substantially as shown. A user controls the system 10 by way of a user interface 16 (e.g., graphical user interface display, keyboard, mouse, etc.) which communicates with the computer and control system 14. Accordingly, the computer and control system 14 generates control signals 13a for the detector cassette 12 which provides image data signals 13b in return. (As desired, one display monitor could be used to selectively display both fluoroscopic and radiographic images, as well as the graphical user interface display image, e.g., all images could be displayed simultaneously in a "windowed" format, or either a fluoroscopic image or a radiographic image could be displayed along with a pull down menu bar, which menu bar constitutes the graphical user interface providing for selection of fluoroscopic or radiographic imaging.)

Following processing of such image data, the computer and control system 14 provides fluoroscopic image data 15a or radiographic image data 15b for display on a fluoroscopic display 18a or a radiographic display 18b, respectively, depending upon the selected mode of operation. The fluoroscopic display 18a preferably employs a phosphor which has a relatively short persistence time, thereby reducing unwanted ghost images when observing motion in the sequence of displayed images. The radiographic display 18b preferably employs a phosphor which yields a bluish tint to gray levels and has a relatively long persistence time, thereby replicating the bluish tint typically found in standard medical X-ray film images and reducing unwanted flicker in the displayed image.

Figure 2:
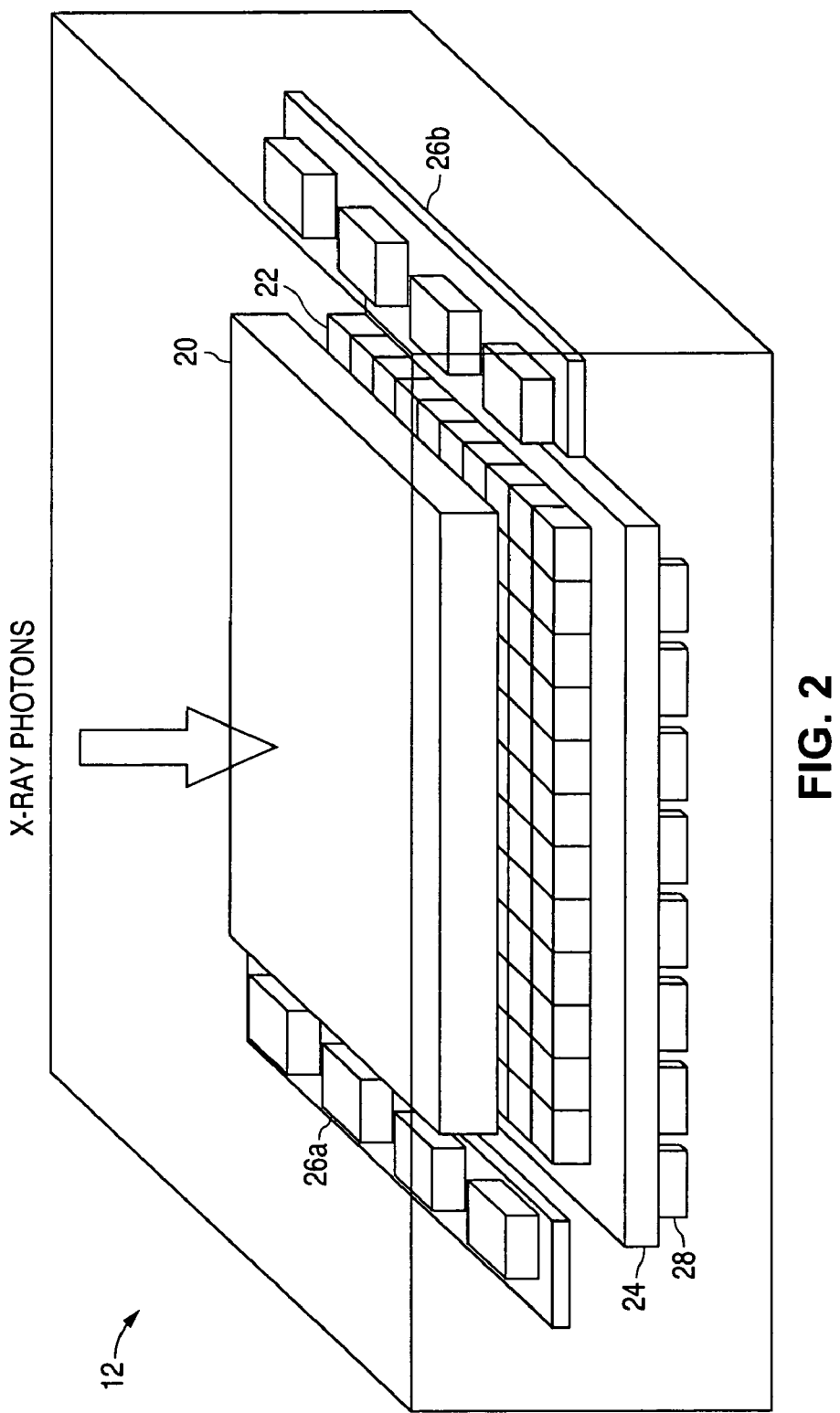
FIG. 2 is an exploded perspective view of an X-ray detector cassette for an X-ray imaging system in accordance with the present invention.

Referring to FIG. 2, the detector cassette, or receptor, 12 is similar in external appearance to the typical cassette which contains standard medical X-ray film and is, therefore, highly mobile and easy to use as required for a radiographic mode of operation. A scintillation layer 20, e.g., of cesium iodide (CsI), absorbs and converts impinging X-ray photons to visible light photons for detection by photosensitive elements within the detector array 22, e.g., of amorphous silicon (a-Si). The thickness of the scintillation layer 20 is selected so as to absorb sufficient X-ray photons and produce sufficient visible photons so as to generate an adequate SNR for fluoroscopic operation. Similarly, the columns, or "needles," of the crystalline CsI are selected so as to have diameters sufficiently small to support the spatial resolution sampling desired for radiographic operation.

The detector array 22 is designed in accordance with well known techniques into a two dimensional array of microscopic squares referred to as picture elements, or "pixels." Each pixel is composed of an addressable photosensitive element, such as a photodiode and switching transistor combination. As discussed in more detail below, each pixel is accessed in accordance with drive signals from off-array driver circuit assemblies 26a, 26b which provide addressing control signals. In accordance with well known techniques, the lateral dimensions of the photodiodes are made sufficiently small to provide the desired spatial resolution imaging for radiographic operation and the capacitance of the photodiodes is designed to be sufficiently large to provide the desired signal handling capacity for accommodating the largest signal produced during radiographic operation.

The pixel data accessed by the driver circuits 26 are read out by a receiver, or readout, circuit assembly 28, as discussed in more detail below. The receiver circuit assembly 28 and detector array 22 are mounted on opposing sides of a base plate 24. (The receiver circuit assembly 28 is placed beneath the array 22 so as to minimize the lateral size of the detector cassette 12 and thereby make the detector cassette 12 approximately the same size as a film cassette. If so desired, the driver circuits 26 can also be placed beneath the array 22.)

Figure 3:
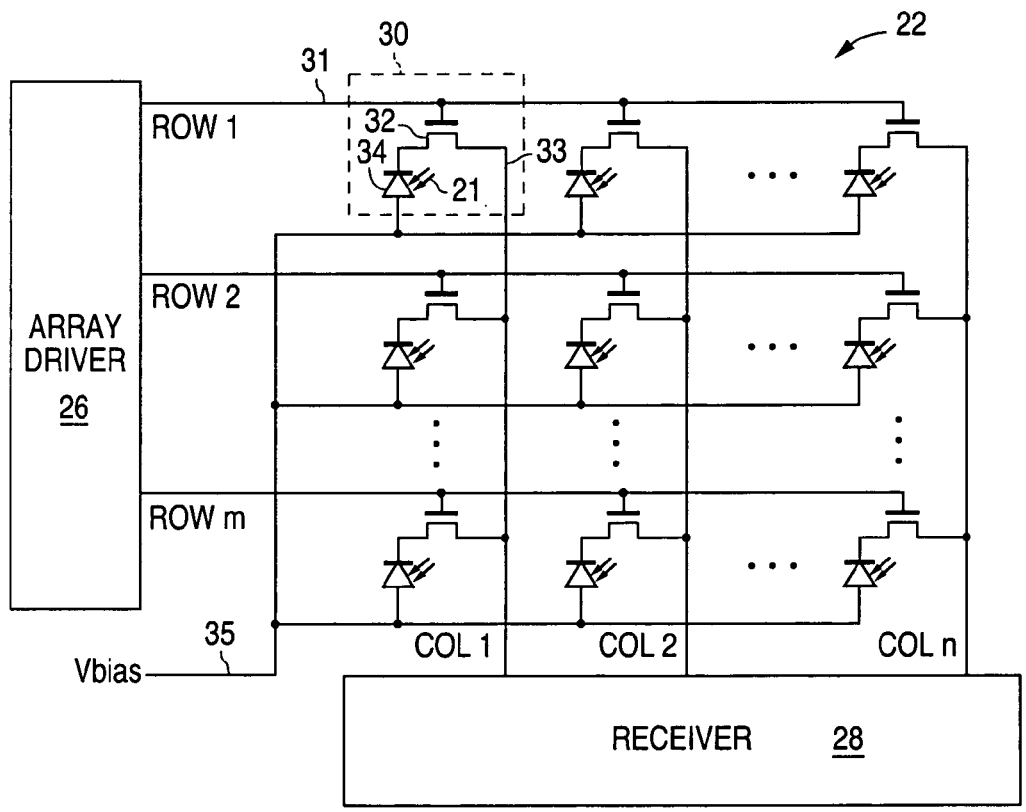
FIG. 3 is a schematic diagram of a portion of the detector array of FIG. 2.

Referring to FIG. 3, the detector array 22, as noted above, is composed of a two dimensional array, or matrix, of photosensitive pixels 30 which, in a preferred embodiment, include a switching transistor 32 and a photodiode 34. The anode of the photodiode 34 is biased by a biasing voltage 35 to establish a capacitance for storing electrical charges which accumulate due to the reception of incident light 21 from the scintillation layer 20 (FIG. 2). When the pixel 30 is accessed, a row address signal 31 from the array driver circuit 26 (discussed in more detail below) drives the gate of the switching transistor 32 (TFT), thereby providing a column data signal 33 representing the stored charge from the photodiode 34. This signal 33 is received and buffered by a charge sensitive amplifier within the receiver circuit assembly 28 (discussed in more detail below).

Each row address signal 31 is asserted for a predetermined period of time, referred to as "pixel discharge time." During assertion of each row address signal 31, the signal 33 from each pixel along that row is transmitted via the column data lines to the receiver circuit assembly 28 where the signal 33 on each data line is received and buffered by a corresponding charge sensitive amplifier (discussed in more detail below). Hence, an entire row of image data is captured in one pixel discharge time period. With each subsequent pixel discharge time period, a subsequent row of image data is captured. At the end of a "frame time" period, the entire image has been captured. In this manner, each pixel contained in the entire active detection area is sampled individually.

Based upon the foregoing, and in accordance with the more detailed discussions of the driver 26 and receiver 28 circuit assemblies which follow, it can be seen that the pixel array supports multiple modes of operation. For example, during radiographic operation, the pixel data is sampled on a pixel-by-pixel basis as discussed above. However, during fluoroscopic operation, pixel data access can be accelerated, albeit with a reduction in spatial resolution. This can be done by combining, or "binning," multiple pixels to produce "super pixels." For example, a two-by-two pixel subset in which two rows and columns of pixels are combined can be created by addressing two adjacent rows and two adjacent columns of pixels at one time, with the driver circuit assembly 26 performing the simultaneous row addressing and the receiver circuit assembly 28 performing the column line signal combining. Hence, while the spatial resolution is reduced accordingly, significantly less time will be required to capture the image, thereby allowing fluoroscopic imaging to be performed.

This use of super pixels can also be done in a more selective manner. For example, image acquisition in a fluoroscopic magnification mode can be performed when only a portion of the active detection area is of interest. During such operation, the rows outside the region of interest are addressed at a rapid rate or skipped entirely, while the rows within the region of interest are addressed at a slower rate. The overall time to sequence through or skip past all of the rows, i.e., the frame time, can remain equal to the frame time associated with the fluoroscopic normal mode. However, due to the increased time available within the region of interest, the super pixels within such region can be reduced in size, thereby increasing the spatial resolution. (Appropriate combining of column line signals is also used accordingly.) Hence, the smaller the size of the super pixel in the region of interest, the higher the apparent magnification. (A smaller area of the detector is captured when operating in fluoroscopic magnification mode than when operating in fluoroscopic normal mode, but the display area remains the same, thereby producing an apparent magnification.)

Figure 4:
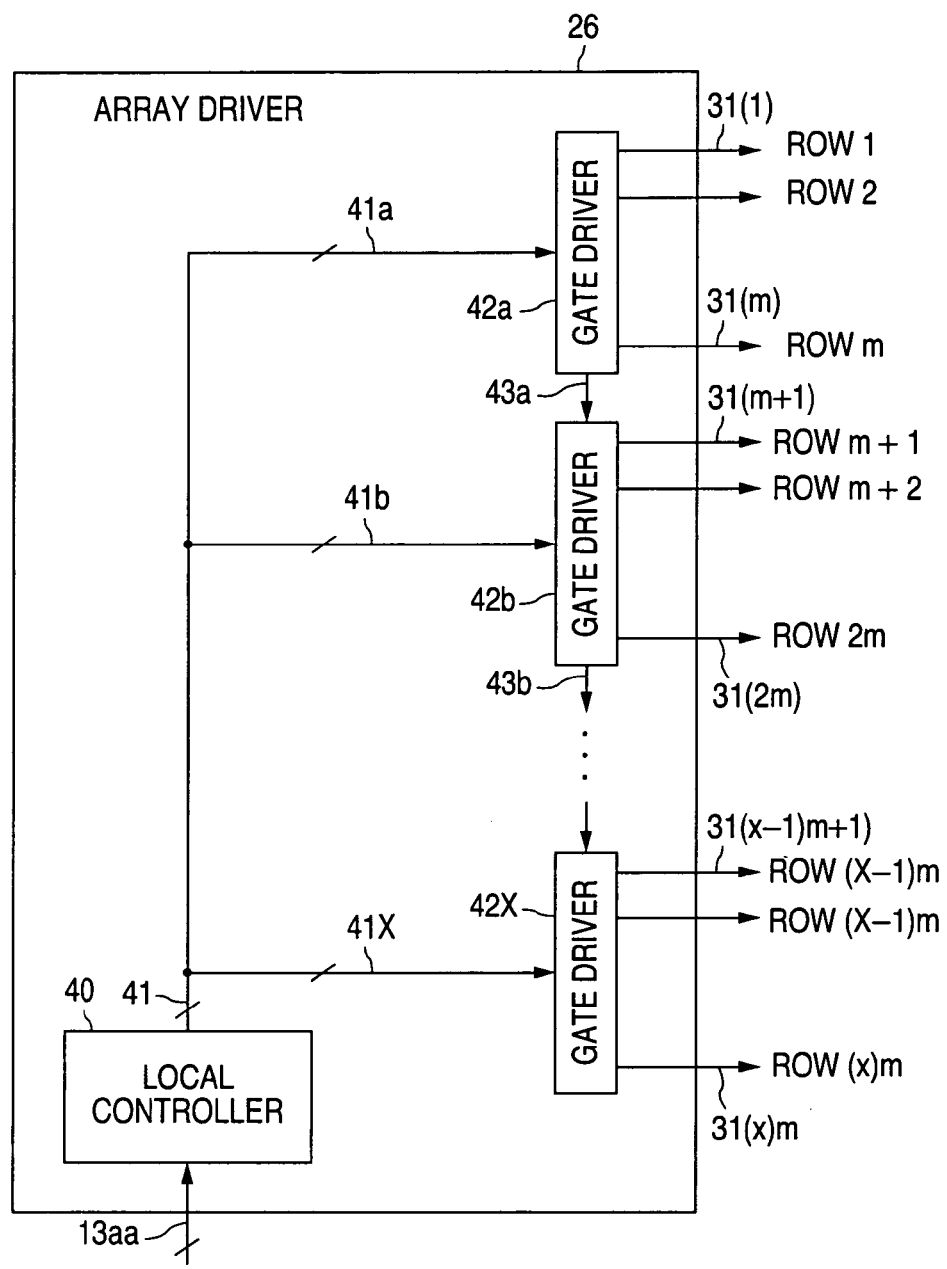
FIG. 4 is a functional block diagram of the array driver circuit assemblies of FIG. 2.

Referring to FIG. 4, the driver circuit assembly 26 includes a local controller 40 for receiving control signals 13aa from the computer and control system 14 (FIG. 1), plus a series of gate drivers 42 for providing the row addressing signals 31. These gate drivers 42 can be operated in the manner of shift registers or, alternatively, be individually programmed as desired according to the mode of operation using the control signals 41 from the local controller 40. For example, during radiographic operation, the driver circuits 42 can be programmed such that the row 1 addressing signal 31 (1) is asserted while the remaining row addressing signals are de-asserted. Immediately following the next line synchronization cycle, the row 1 signal is de-asserted and the row 2 signal is asserted, while the remaining row signals are de-asserted. This successive assertion and de-assertion of signals is repeated until all rows have been addressed. During fluoroscopic operation, the foregoing assertion and de-assertion sequence is repeated, with the exception that multiple adjacent row address signals are asserted at one time for creating super pixels, as discussed above.

Figure 5:
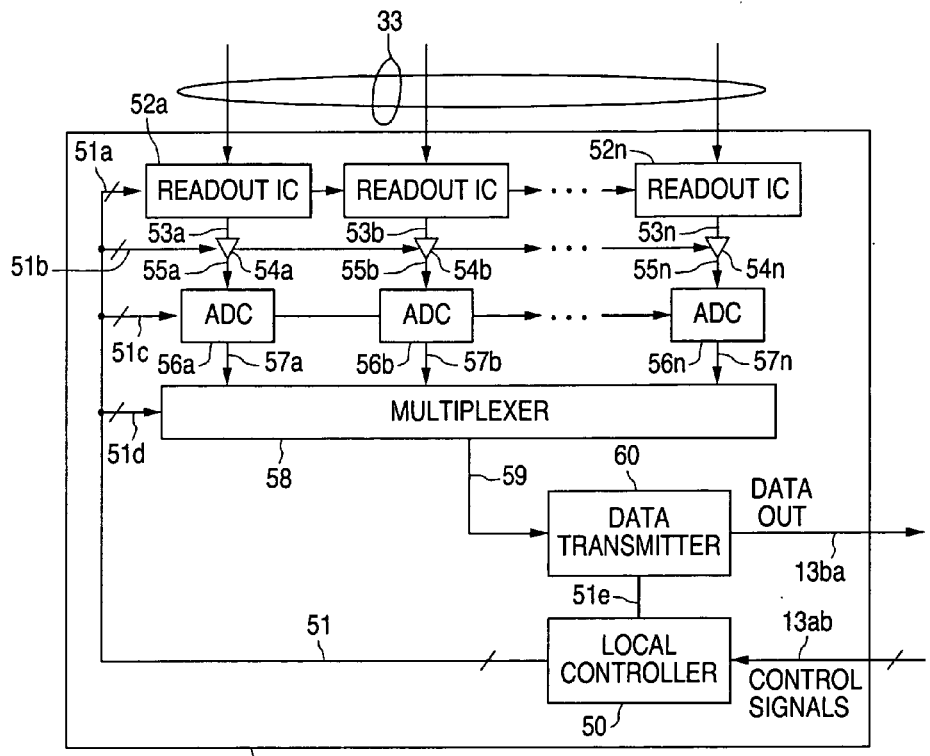
FIG. 5 is a functional block diagram of the receiver circuit assembly of FIG. 2.

Referring to FIG. 5, the receiver circuit assembly 28 includes a local controller 50 for receiving control signals 13ab from the computer and control system 14 (FIG. 1) and generating local control signals 51. In accordance with its local control signals 51a, a number of readout circuits 52 (discussed in more detail below), the number of which depends upon the number of columns to be read out from the detector array 22, receives the column data signals 33. The outputs 53 from the readout circuits 52 are buffered by respective transimpedance amplifiers 54. These transimpedance amplifiers 54 are controlled by local control signals 51b for purposes of controlling their offset and gain characteristics (discussed in more detail below). The buffered column data signals 55 are converted by analog-to-digital converters (ADCs) 56. The resulting digitized column data signals 57 are then multiplexed by a multiplexor. The resulting multiplexed data signals 59 are buffered by a data transmitter 60 for transmission to the computer and control system 14.

The control signals 51b for the transimpedance amplifiers 54 are used to selectively optimize the offset and gain characteristics of the amplifiers 54. This allows the amplifiers 54 to be biased to match the respective output signal ranges of the amplifiers 54 to the input signal ranges of the corresponding ADCs 56.

Figure 6:
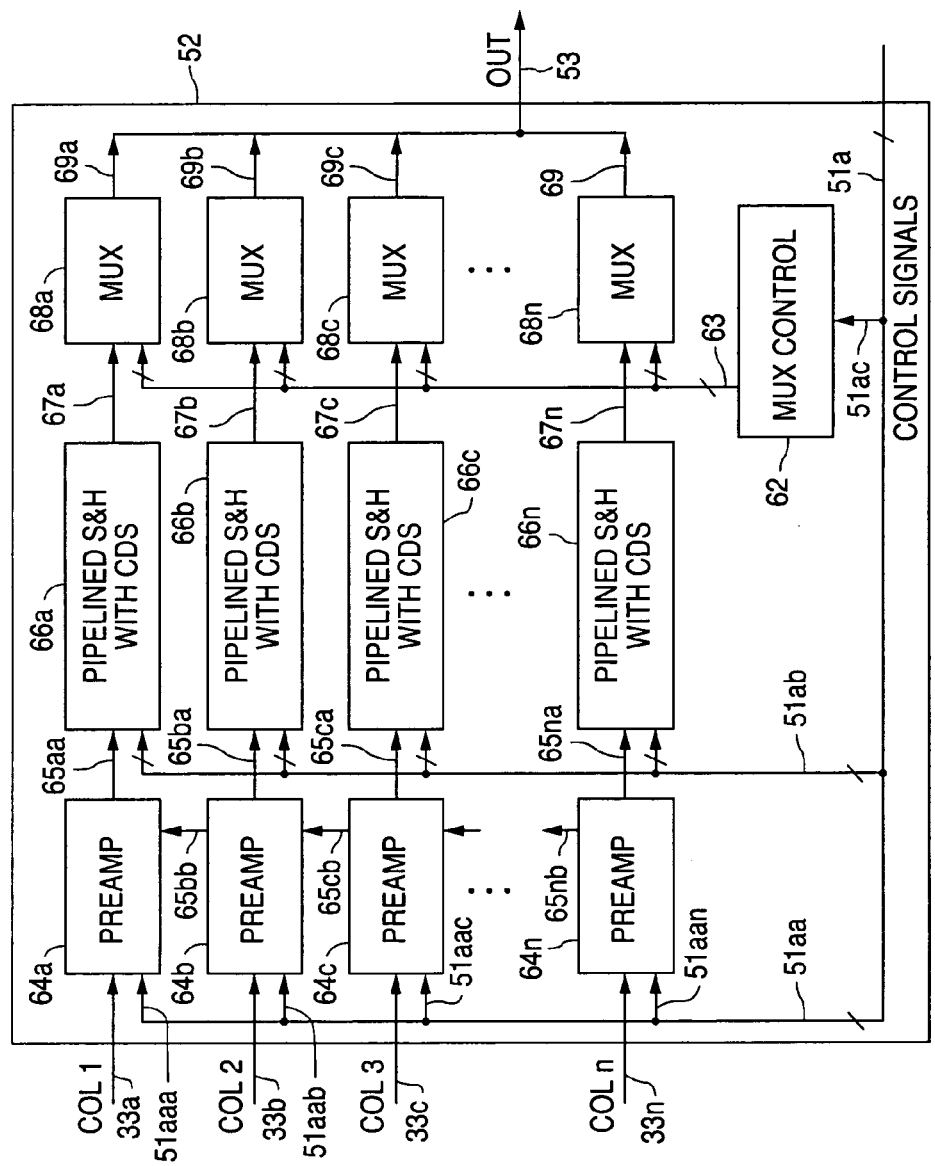
FIG. 6 is a functional block diagram of the readout circuits in the receiver circuit assembly of FIG. 5.

Referring to FIG. 6, the readout circuits 52 collectively include multiple input preamplifiers 64, pipelined sample and hold circuits 66 and output multiplexors 68, interconnected substantially as shown. The control signals 51a from the local controller 50 (FIG. 5) control the preamplifiers 64, pipelined sample and hold circuits 66 and a multiplexor controller 62 which, in turn, controls the multiplexors 68 via multiplexor control signals 63. The preamplifiers 64 receive the column data signals 33 with charge sensitive amplifiers and provide the aforementioned binning capability for creating super pixels (in conjunction with the multiple row addressing capability of the array driver circuit 26 (FIG. 4) as discussed above). The charge sensitive amplifiers are discussed in more detail in U.S. Pat. No. 6,084,461, entitled "Charge Sensitive Amplifier With High Common Mode Signal Rejection," the disclosure of which is incorporated herein by reference. (The pixel binning capability provided by the preamplifiers is discussed in more detail below in connection with FIG. 7.)

The buffered output signals 65aa, 65ba, 65ca, from the preamplifiers 64, are sampled using correlated double sampling by the pipelined sample and hold circuits 66 in accordance with their respective control signals 51ab. These pipelined sample and hold circuits 66 are described in more detail in U.S. Pat. No. 5,872,470, entitled "Pipelined Sample and Hold Circuit With Correlated Double Sampling," the disclosure of which is incorporated herein by reference.

The sampled data signals 67 are multiplexed by their respective multiplexors 68 to provide the final output signal 53. These multiplexors 68 operate in an analog current mode and are described in more detail in U.S. Pat. No. 5,801,571, entitled "Current Mode Analog Signal Multiplexor," the disclosure of which is incorporated herein by reference.

Figure 7:
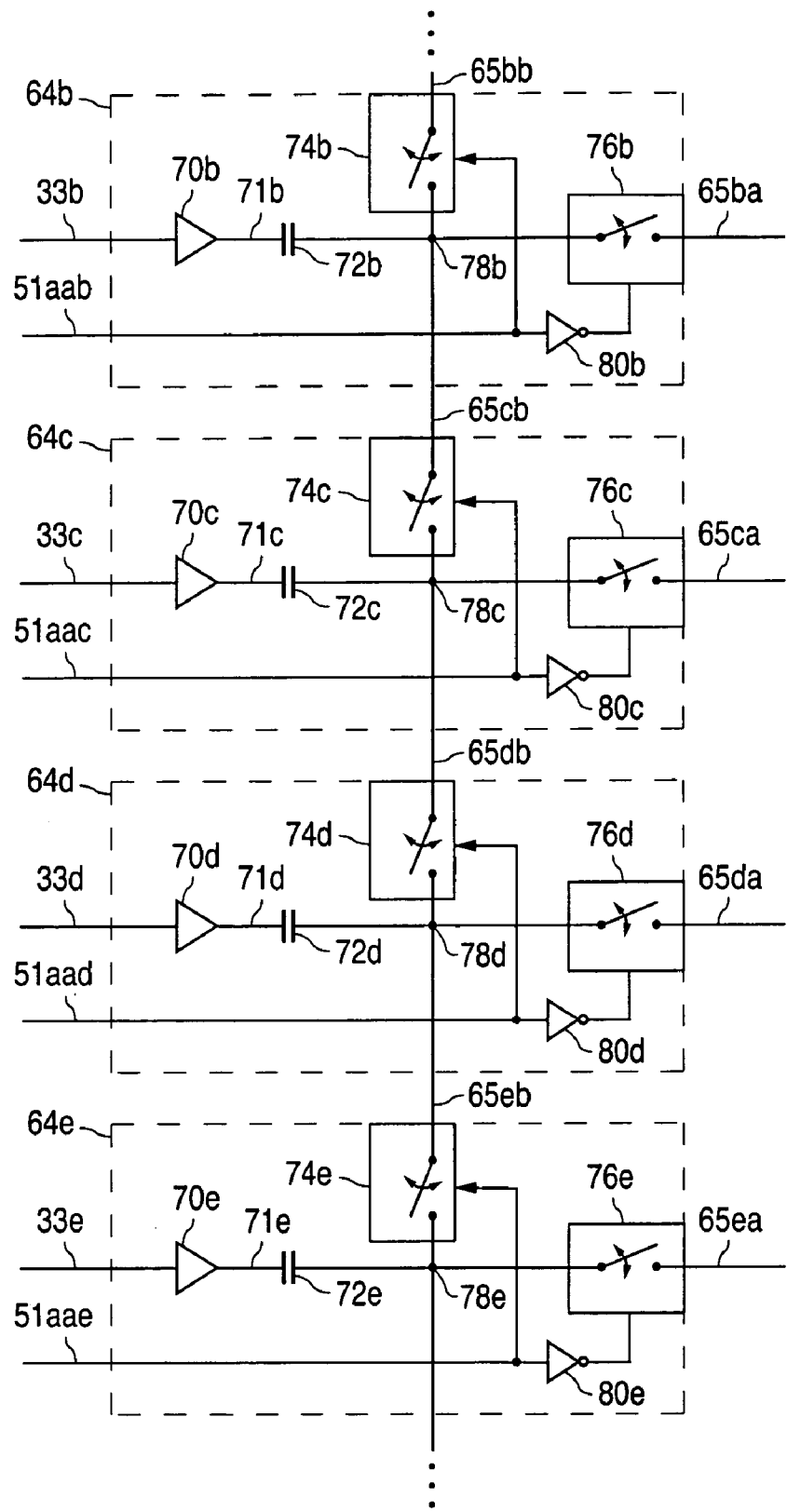
FIG. 7 is a simplified schematic diagram of several adjacent preamplifier circuits in the readout circuit of FIG. 6.

Referring to FIG. 7, the aforementioned pixel binning capability with respect to the column data can be described as follows. For purposes of this explanation, the second 64b, third 64c and fourth 64d preamplifier circuits are illustrated to represent the interconnection among adjacent preamplifiers 64. Internal to each preamplifier 64 is the aforementioned charge sensitive amplifier 70 which receives the column data signal 33. The buffered column data signal 71 is coupled by a series coupling capacitor 72 to a summing node 78 for selectively being summed with the buffered and capacitively coupled column data signal from its adjacent preamplifier circuit 64. For example, if one-by-two super pixels were being used, then the third and fourth pixels would be binned together by appropriately asserting and de-asserting the control signals in signal sets 51aac and 51aad (and their inverse equivalents via inverters 80c and 80d) so that switches 74c, 74e and 76d are opened and switches 74d and 76c are closed. Accordingly, the buffered and capacitively coupled data signal 65db from the fourth preamplifier 64d is summed with that of the third preamplifier 64c at its summing mode 78c for outputting as binned pixel data signal 65ca.

During the imaging process, the X-rays can be either pulsed or continuous. Continuous X-rays are on continuously during the entire frame time associated with the display device (e.g., for the entire approximately 33 milliseconds for a 30 frame per second display rate). Pulsed X-rays are delivered only during a portion of the frame time, and can be preferable to continuous X-rays since motion artifacts due to patient motion during the panel scanning are minimized. However, pulsed-X-rays delivered during the detector, or receptor, readout (scanning) cause an offset shift within the data signals, thereby creating a band artifact within the image display. Accordingly, pulsed X-rays are generally delivered during the non-scanning portion of the frame time. To increase the available scanning time while also maximizing the time available for delivering the X-ray beam pulse, split data line architectures have been used to allow parallel scanning of multiple portions of the detector array.

Figure 8:
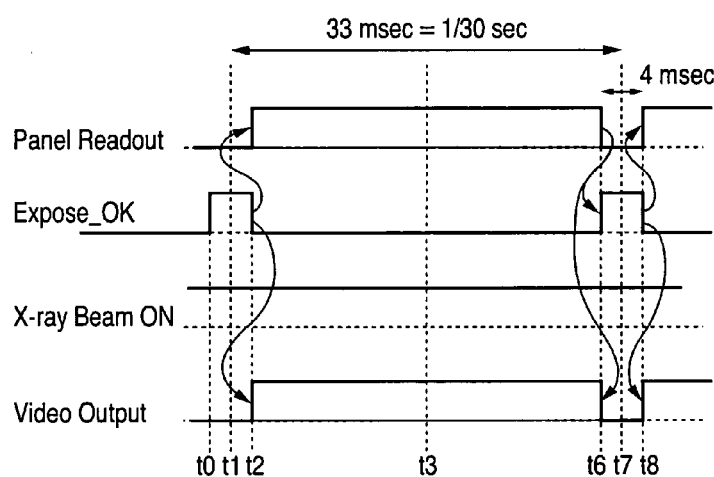
FIG. 8 is a signal timing diagram for a progressive pixel data scan readout with continuous X-rays.

Referring to FIG. 8, the typically progressive scanning of an X-ray receptor using a continuous X-ray beam can be represented with a signal timing diagram as shown. The X-ray beam is on continuously, while panel readout, i.e., reading of the individual pixel data signals, occurs within the scanning frame boundaries defined by time points t1 and t7. Often a scanning enable signal of some kind, such as that represented by the expose_ok signal, is present in the system; however, with continuous X-ray radiation, such signal plays virtually no role, other than perhaps to determine the time interval in which the video output is made available (e.g., via appropriate signal conversion during time interval t2–t6).

It should be noted that the timing diagrams include lines with arrows between various leading and trailing edges of the signals depicted; however, unless otherwise indicated, such lines are merely to identify relative "before versus after" timing relationships between the signals and do not necessarily indicate a synchronous or other form of cause and effect relationship between such signals.

Figure 9:
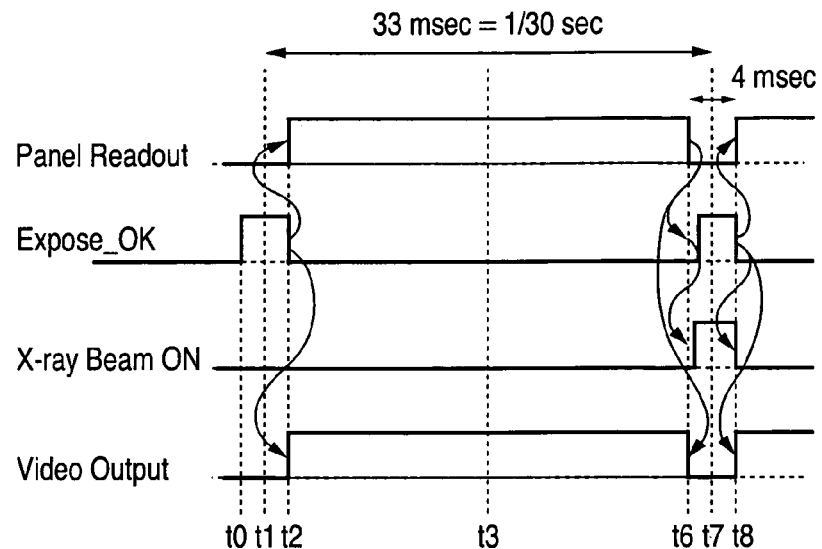
FIG. 9 is a signal timing diagram for a progressive pixel data scan readout with pulsed X-rays.

Referring to FIG. 9, a progressive receptor panel scan using pulsed X-rays can be represented as shown. Again, panel readout occurs within the scanning time frame t1–t7 with the scanning and video output being coincident during the time interval t2–t6. In this situation, the expose_ok signal serves to enable, or trigger, the X-ray beam during time interval t6–t8.

Figure 10:
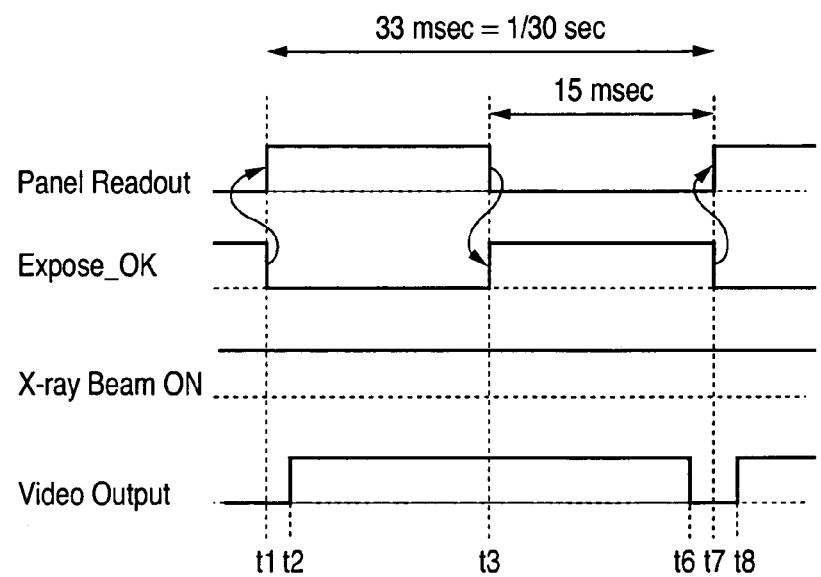
FIG. 10 is a signal timing diagram for a continuous fluoroscopy pixel data scan with a split data line readout.

Referring to FIG. 10, a fluoroscopy mode of operation using continuous X-rays can be represented as shown. In this mode of operation, panel readout occurs for approximately one half of the scanning frame time as defined by time interval t1–t3. The output video signals are available during time interval t2–t6.

Figure 11:
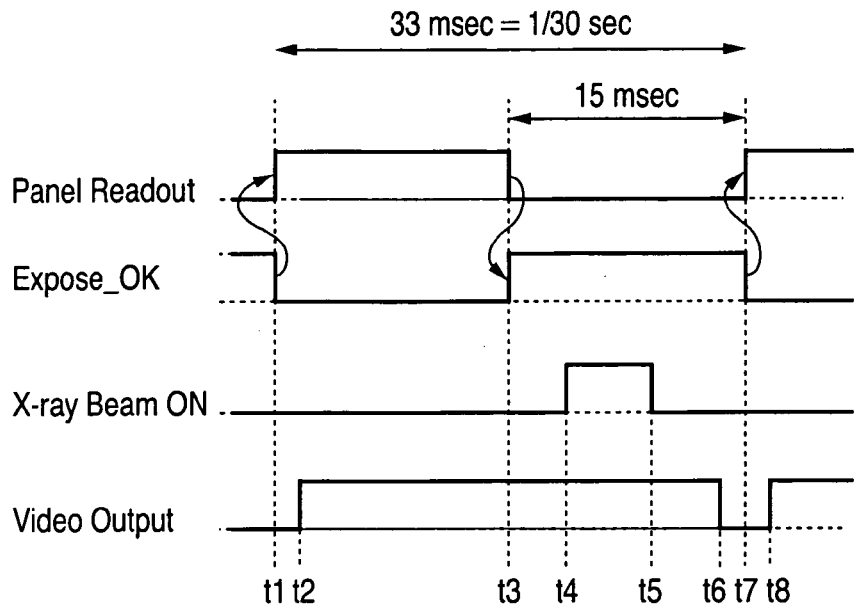
FIG. 11 is a signal timing diagram for a pulsed fluoroscopy pixel data scan with a split data line readout.

Referring to FIG. 11, a fluoroscopy mode of operation using pulsed X-rays can be represented as shown. Again, panel readout occurs for approximately half of the scanning frame as defined by time interval t1–t3. During this time interval t1–t3, the expose_ok signal is de-asserted, corresponding to no application of the X-ray beam. During the remaining time within the scanning frame, as defined by time interval t3–t7, the expose_ok signal is asserted, corresponding to application of the X-ray beam as desired, e.g., during time interval t4–t5. The pixel data is made available for display via the video output during time interval t2–t6. This mode of operation, as represented, allows the entire panel to be read out during time interval t1–t3 at the desired fluoroscopy resolution and is made possible by the use of a split data line so that two halves of the receptor panel can be read out simultaneously in parallel, thereby maintaining the 30 frame per second rate.

When operating in a magnification, or "zoom," mode of operation, scanning of the region of interest (ROI) on the receptor panel is most desirably done at full resolution and at the maximum scanning frame rate. However, because row selection during scanning is typically done with a shift register topology to drive the gates of the individual pixel cells (FIG. 4), the unused rows, i.e., those pixels within the rows not intended for display, must be scanned in order to reach the pixels of interest. An issue that arises from this is that of what is to be done with the unused pixels. One possibility is to not read, and therefore not discharge, the unused pixels, or do a fast, and therefore incomplete, discharge of the unused pixels. Alternatively, the unused pixels could be read (discharged) during the expose_ok time interval, thereby allowing for a full discharge.

Accelerated scanning, i.e., using an increased scanning clock rate and scanning pulses (row address signal 31, FIG. 3) of reduced signal assertion time duration (i.e., shorter "pixel discharge time"), of the unused pixels allows charge to accumulate on the pixels, resulting in a relatively permanent change in their respective offset or background data values. Such changes in offset values can cause the image normalization to fail when the panel is returned to a full field of view mode, such as that used for normal fluoroscopy or radiography operation.

On the other hand, accelerated discharging of the unused pixels can minimize the risk of charge buildup, but charge buildup can occur depending upon the level, or dose, of X-ray radiation to which the receptor is exposed, as well as the particular pixel scanning parameters. Additionally, such accelerated discharging requires more complicated clocking techniques, e.g., using multiple frequency clocks.

By using beam-on scanning, i.e., where the unused pixels are scanned contemporaneously with application of the X-ray radiation to the receptor, the unused pixels are fully discharged during each data frame, and consistent clocking and pixel readout can be maintained. (The following discussion of magnification, or "zoom," mode of operation refers to the use of pulsed X-rays during the imaging process. However, as indicated above, it should be understood that either pulsed or continuous X-rays can be used.)

Figure 12:
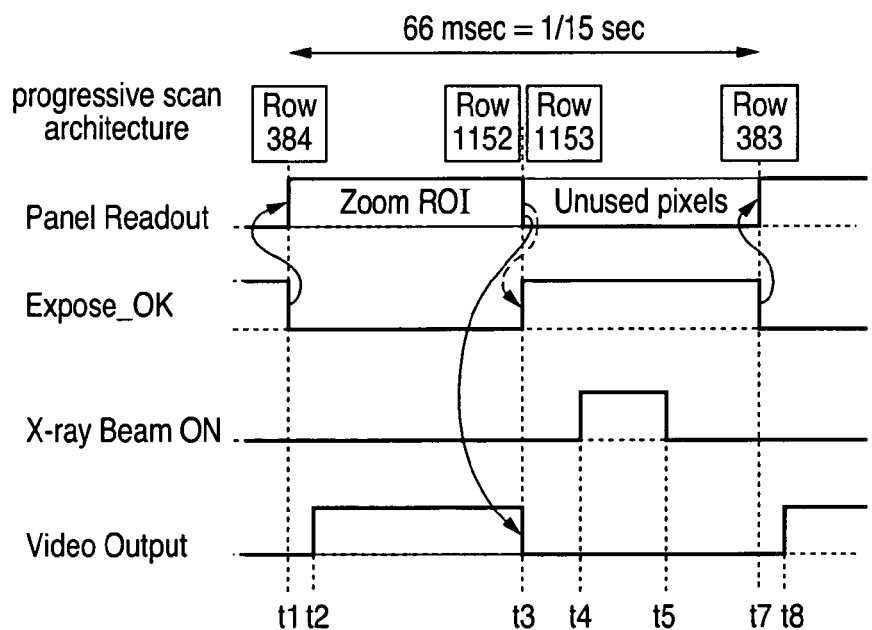
FIG. 12 is a signal timing diagram for a magnification mode pixel data scan readout using X-ray beam-on scanning in accordance with one embodiment of the presently claimed invention.

Referring to FIG. 12, this last alternative can be represented as shown. During time interval t1–t3, the expose_ok signal is de-asserted and the X-ray beam is off. During this time interval t1–t3, the region of interest is scanned, e.g., row 384 through row 1152. Subsequently, during time interval t3–t7, the expose_ok signal is asserted, thereby allowing activation of the X-ray beam during scanning of the unused pixels, e.g., row 1153 through row 383 (i.e., rows 1153–1536 and rows 1–383).

Figure 13:
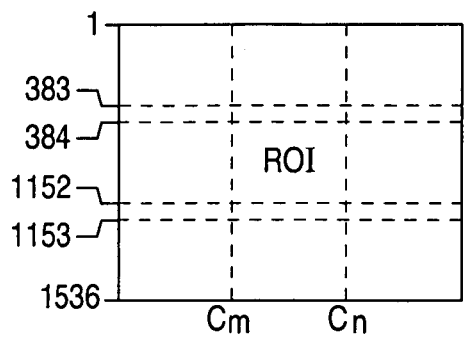
FIG. 13 illustrates how the scanning mode of FIG. 12 captures the image region of interest.

Referring to FIG. 13, this scanning mode can be visualized in terms of the resultant video image to be displayed on the display device. As discussed above, during de-assertion of the expose_ok signal, rows 384–1152 are scanned for accessing the corresponding pixel data and making it available for video display as desired (e.g., in conformance with the discussion above concerning FIGS. 3, 4, 5, 6 and 7). During assertion of the expose_ok signal, the X-ray beam is activated (e.g., during time interval t4–t5) and the unused pixels, i.e., those corresponding to the image regions outside the region of interest, are scanned for rows 1153–1536 and rows 1–383.

Up to this point, this makes available all of the pixel data corresponding to the image from row 384 through row 1152. In the event that less than the full width of this image area is desired for display, only the desired pixels within these rows, e.g., between pixel columns Cm and Cn (with such pixel columns Cm, Cn being defined as desired anywhere between the left-most and right most column of the image display) need be converted to the appropriate video signals for display.

As indicated in FIG. 12, accessing the pixels of interest and the unused pixels in this manner causes the scanning frame rate to be reduced, e.g., by half. A higher scanning rate can be maintained, however, if a split data line structure is used so as to allow for reading out of pixels from multiple regions of the receptor panel simultaneously.

Figure 14:
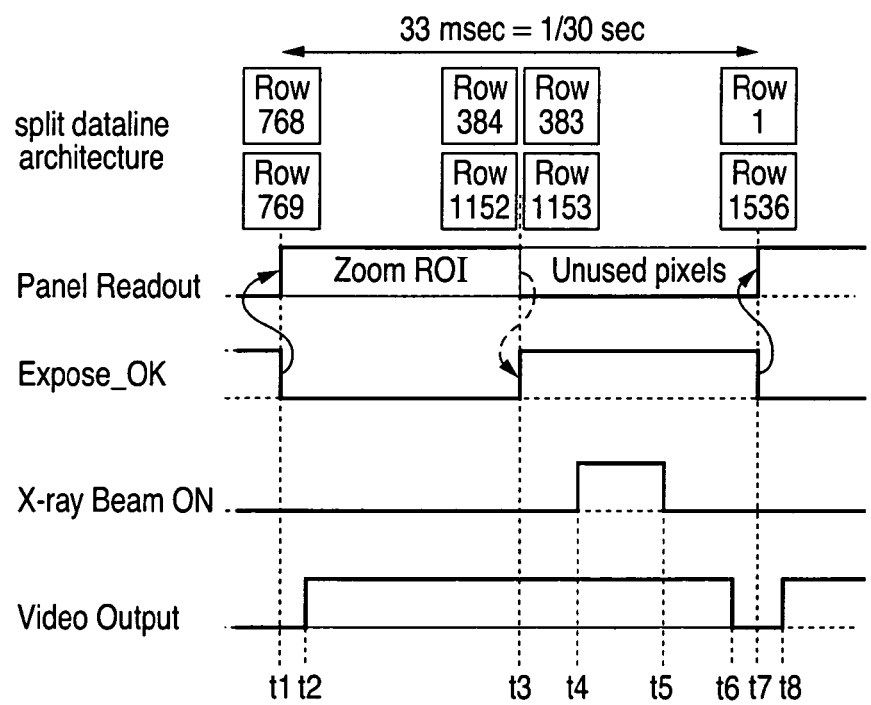
FIG. 14 is a signal timing diagram for a magnification mode pixel data readout using X-ray beam-on scanning in accordance with another embodiment of the presently claimed invention.

Referring to FIG. 14, reading out the pixel data in a magnification mode of operation using a split data line architecture can be represented as shown. As before, panel readout occurs during de-assertion of the expose_ok signal (time interval t1–t3), while the unused pixels are scanned during assertion of the expose_ok signal (time interval t3–t7) and activation of the X-ray beam (during time interval t4–t5). However, the original data scanning frame rate is maintained by using a split data line architecture such that multiple groups of pixel rows are read out during both panel readout time intervals t1–t3, t3–t7.

Figure 15:
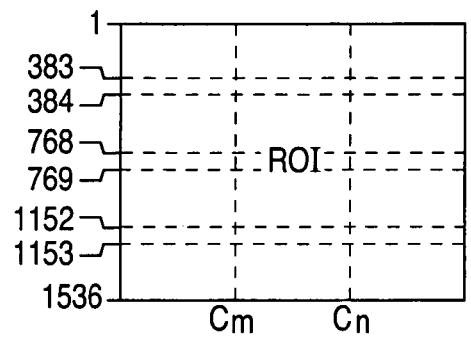
FIG. 15 illustrates how the scanning mode of FIG. 14 captures the image region of interest.

Referring to FIGS. 15 and 14, for example, the pixels corresponding to the region of interest can be read out during time interval t1–t3 by reading the data pixels corresponding to image rows 768–384 and rows 769–1152 simultaneously. Similarly, the unused pixels can be read out during time interval t3–t7 by reading the data pixels corresponding to image rows 383-1 and rows 1153–1536 simultaneously. For example, as indicated in FIG. 14, during panel readout of the region of interest, rows 768 and 769 can be read simultaneously, followed by simultaneous reading out of rows 767 and 770, and so on through simultaneous readout of rows 384 and 1152. Similarly, during scanning of the unused pixels, rows 383 and 1153 can be read out simultaneously, followed by simultaneous reading of rows 382 and 1154, and so on through simultaneous readout of rows 1 and 1536.

It should be understood that other combinations of pixel rows within and without the region of interest can be read simultaneously depending upon the specific split data line structure. It should be further understood that the order in which the various rows of pixel data are read out is not limited to the examples discussed above. For example, for the scanning technique of FIGS. 12 and 13, the scanning order in the region of interest can be either row 384 through row 1152 or row 1152 through row 384, and the scanning for the unused pixels can be ordered as row 1153 through row 383 (i.e., rows 1153–1536 and rows 1–383), or as row 383 through row 1153 (i.e., rows 383-1 and rows 1536–1153), or according to some other order as desired. Similarly, for the scanning technique of FIGS. 14 and 15, the scanning order in the region of interest can be as either row 768 through row 384 and row 769 through row 1152 simultaneously, respectively, or row 384 through row 768 and row 1152 through row 769 simultaneously, respectively, and the scanning order for the unused pixels can be ordered as row 383 through row 1 and row 1153 through row 1536 simultaneously, respectively, or as row 1 through row 383 and row 1536 through row 1153 simultaneously, respectively, or according to some other order as desired.

Figure 16:
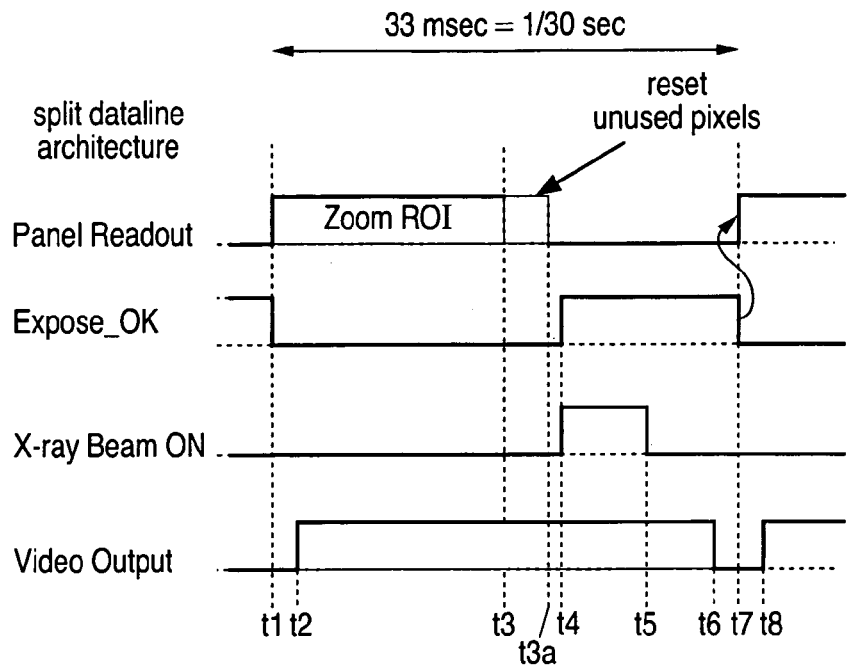
FIG. 16 is a signal timing diagram for a magnification mode pixel data readout using X-ray beam-on scanning in accordance with still another embodiment of the presently claimed invention.

Referring to FIG. 16, reading-out the pixel data in a magnification mode of operation using the split data line architecture while using an alternative technique for resetting unused pixels can be represented as shown. As before, panel readout, i.e., scanning of the used pixels (within the region of interest), occurs during de-assertion of the expose_ok signal (time interval t1–t3). However, in this embodiment, the unused pixels are scanned (and, therefore, reset) in an accelerated manner during a time interval t3–t3a following the panel readout interval (time interval t1–t3) and preceding assertion of the expose_ok signal (time interval t4–t7) and activation of the X-ray beam (time interval t4–t5). It will be appreciated that by resetting the unused pixels prior to allowing exposure to the X-ray beam helps to ensure that no, or at least minimal, signal artifacts will remain or otherwise be present in the unused pixels which could introduce noise or some form of corrupted pixel data in some way. (It should be understood that such resetting of the unused pixels can also be performed while contemporaneously allowing exposure to the X-ray beam, e.g., where time point t4 precedes time point t3a; however, as noted, higher levels of signal artifacts may remain in the unused pixels.)

Figure 17:
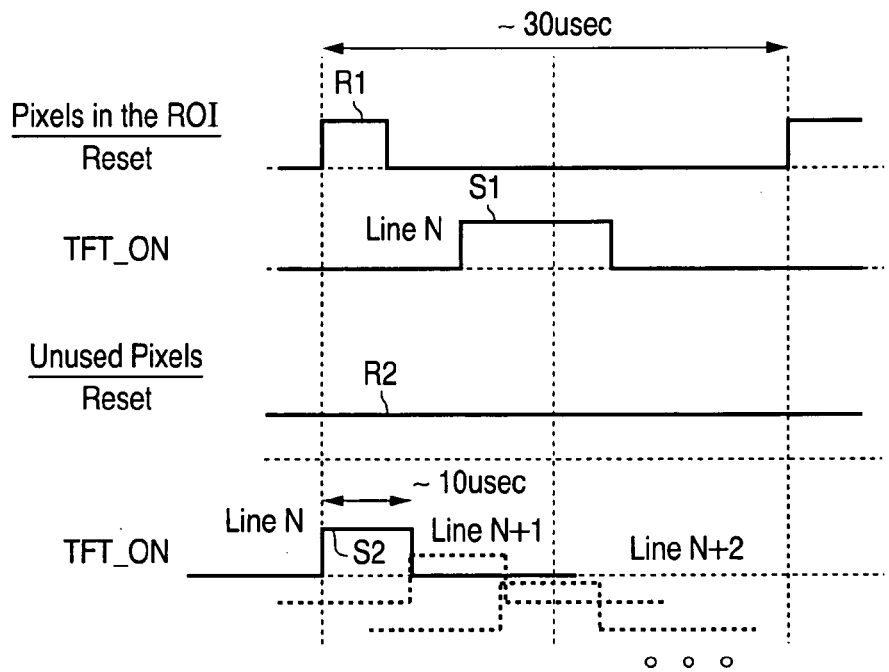
FIG. 17 is a signal timing diagram illustrating timing relationships among signals used when resetting and scanning used pixels (i.e., within the region of interest) and unused pixels.

Referring to FIG. 17, the relative timings between the resetting and scanning of the used pixels and unused pixels can be described as follows. For the pixels in the region of interest (time interval t1–t3), a reset pulse R1 is applied to the charge integrators within the readout circuits 52 (FIG. 5), following which a series of scanning pulses S1 are applied to each line, or row, of pixels (row address signal 31, FIG. 3) to read out the pixel data for the used pixels. Meanwhile, for the unused pixels (time interval t3–t7), the reset signal R2 is preferably (though need not necessarily be) on at least for the duration of the reset interval (time interval t3–t3a).

During such reset interval, scanning pulses S2 (row address signal 31, FIG. 3) of substantially normal time durations are applied sequentially in accelerated succession to each row, or line, of pixels to read out the pixel data for the unused pixels (even though such pixel data will not be further processed due to the contemporaneous resetting of the charge integrators). Such pulses S2 are applied more rapidly, i.e., with less than normal time between successive pulses, since no time need be allowed for subsequent processing of the pixel data, thereby resulting in a higher effective data rate; however, the pixel discharge times (time duration of signal assertion) of such pulses S2 remain substantially equal to normal pixel discharge times (pixel discharge times for the scanning pulses S1 for the used pixels). As noted above, this ensures that the individual photo diodes 34 (FIG. 3) have been discharged, as well as the charge integrators within the readout circuits 52 (FIG. 5).

Various other modifications and alternations in the structure and method of operation of this invention will be apparent to those skilled in the art without departing from the scope and the spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A method for providing X-ray image data signals corresponding to a selected portion of a two-dimensional image at an enhanced image resolution, comprising:
    exposing at least a portion of an X-ray receptor to an amount of X-ray radiation corresponding to said two-dimensional image during at least a first portion of a second time interval but not during at least a first portion of a first time interval;
    reading out, from said X-ray receptor at a first data rate during at least a second portion of said first time interval, a first plurality of pixel data signals corresponding to at least a first portion of said two-dimensional image and having a first pixel discharge time associated therewith; and
    reading out, from said X-ray receptor at a second data rate during at least a second portion of said second time interval, a second plurality of pixel data signals corresponding to at least a second portion of said two-dimensional image and having a second pixel discharge time associated therewith, wherein said first and second pixel discharge times are substantially equal, and said first and second portions of said two-dimensional image are substantially mutually exclusive.

2. The method of claim 1, wherein said reading out, from said X-ray receptor at a first data rate during at least a second portion of said first time interval, a first plurality of pixel data signals corresponding to at least a first portion of said two-dimensional image and having a first pixel discharge time associated therewith comprises simultaneously reading out first and second portions of said first plurality of pixel data signals corresponding to first and second substantially contiguous subordinate portions of said first portion of said two-dimensional image.

3. The method of claim 2, wherein said reading out, from said X-ray receptor at a second data rate during at least a second portion of said second time interval, a second plurality of pixel data signals corresponding to at least a second portion of said two-dimensional image and having a second pixel discharge time associated therewith comprises simultaneously reading out first and second portions of said second plurality of pixel data signals.

4. The method of claim 1, wherein said first plurality of pixel data signals corresponds to a matrix of image pixels including a plurality of rows of image pixels, and further comprising converting said first plurality of pixel data signals to a plurality of video image signals suitable for displaying via an image display device said at least a subordinate portion of said first portion of said two-dimensional image by converting a portion of said first plurality of pixel data signals corresponding to a selected portion of selected ones of said plurality of rows of image pixels.

5. The method of claim 1, wherein:
    said first and second pluralities of pixel data signals correspond to a matrix of image pixels including first, second and third successive pluralities of rows of image pixels;
    said reading out, from said X-ray receptor at a first data rate during at least a second portion of said first time interval, a first plurality of pixel data signals corresponding to at least a first portion of said two-dimensional image and having a first pixel discharge time associated therewith comprises reading out a plurality of pixel data signals corresponding to said second plurality of rows of image pixels; and
    said reading out, from said X-ray receptor at a second data rate during at least a second portion of said second time interval, a second plurality of pixel data signals corresponding to at least a second portion of said two-dimensional image and having a second pixel discharge time associated therewith comprises reading out a plurality of pixel data signals corresponding to said first and third pluralities of rows of image pixels.

6. The method of claim 5, further comprising converting said first plurality of pixel data signals to a plurality of video image signals suitable for displaying via an image display device said at least a subordinate portion of said first portion of said two-dimensional image by converting a portion of said first plurality of pixel data signals corresponding to a selected portion of selected ones of said second plurality of rows of image pixels.

7. The method of claim 1, wherein:
    said first and second pluralities of pixel data signals correspond to a matrix of image pixels including first, second, third and fourth successive pluralities of rows of image pixels;
    said reading out, from said X-ray receptor at a first data rate during at least a second portion of said first time interval, a first plurality of pixel data signals corresponding to at least a first portion of said two-dimensional image and having a first pixel discharge time associated therewith comprises simultaneously reading out a plurality of pixel data signals corresponding to said second and third pluralities of rows of image pixels; and
    said reading out, from said X-ray receptor at a second data rate during at least a second portion of said second time interval, a second plurality of pixel data signals corresponding to at least a second portion of said two-dimensional image and having a second pixel discharge time associated therewith comprises simultaneously reading out a plurality of pixel data signals corresponding to said first and fourth pluralities of rows of image pixels.

8. The method of claim 7, further comprising converting said first plurality of pixel data signals to a plurality of video image signals suitable for displaying via an image display device said at least a subordinate portion of said first portion of said two-dimensional image by converting a portion of said first plurality of pixel data signals corresponding to a selected portion of selected ones of said second and third pluralities of rows of image pixels.

9. The method of claim 1, wherein said first and second data rates are substantially equal.

10. The method of claim 1, wherein said second data rate is greater than said first data rate.

* * * * *

UNITED STATES PATENT AND TRADEMARK OFFICE
CERTIFICATE OF CORRECTION

PATENT NO. : 7,123,687 B2  Page 1 of 1
APPLICATION NO. : 10/410819
DATED : October 17, 2006
INVENTOR(S) : Colbeth et al.

It is certified that error appears in the above-identified patent and that said Letters Patent is hereby corrected as shown below:

On the cover page,

[*] Notice:   Subject to any disclaimer, the term of this patent is extended or adjusted under 35 USC 154(b) by (49) days Delete the phrase "by 49" and insert --by 146 days--

Signed and Sealed this

Twenty-fifth Day of December, 2007

JON W. DUDAS
*Director of the United States Patent and Trademark Office*